US008674066B2

(12) United States Patent
Nishio

(10) Patent No.: US 8,674,066 B2
(45) Date of Patent: Mar. 18, 2014

(54) PEPTIDE CAPABLE FOR BINDING TO RHODIUM

(71) Applicant: Panasonic Corporation, Osaka, PA (US)

(72) Inventor: Kazuaki Nishio, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/828,022

(22) Filed: Mar. 14, 2013

(65) Prior Publication Data

US 2013/0267040 A1    Oct. 10, 2013

(30) Foreign Application Priority Data

Apr. 10, 2012  (JP) .................................. 2012-088964

(51) Int. Cl.
*C07K 14/00* (2006.01)
(52) U.S. Cl.
CPC ...................................... *C07K 14/00* (2013.01)
USPC ........................................................ 530/324

(58) Field of Classification Search
CPC ....................................................... C07K 14/00
USPC ........................................................ 530/324
See application file for complete search history.

(56) References Cited

U.S. PATENT DOCUMENTS 7,939,307 B2 *   5/2011   Otsuka et al. ................. 435/189

OTHER PUBLICATIONS

Sigal et al. "Effect of Surface Wettability on the Adsorption of Proteins and Detergents" Journal of the American Chemical Society, vol. 120, pp. 3464-3473, 1998.

* cited by examiner

*Primary Examiner* — Julie Ha
(74) *Attorney, Agent, or Firm* — McDermott Will & Emery LLP

(57) ABSTRACT

The present invention provides a novel peptide capable for binding to rhodium. The peptide consists of an amino acid sequence represented by SQMMGHMGHGNMNHMNHG-GKFDFHH (SEQ ID NO: 01).

2 Claims, 4 Drawing Sheets

PEPTIDE CAPABLE FOR BINDING TO RHODIUM

CROSS-REFERENCE TO RELATED APPLICATIONS

This application claims the priority of Japanese Patent Application No.: 2012-088964 filed Apr. 10, 2012, the content of which is incorporated herein by reference.

BACKGROUND OF THE INVENTION

Technical Field

The present invention relates to a peptide capable for binding to rhodium.

SUMMARY

Technical Problem

The purpose of the present invention is to provide a novel peptide capable for binding to rhodium.

Solution to Problem

The present invention is a peptide capable for binding a rhodium, wherein the peptide consists of an amino acid sequence represented by SEQ ID NO: 01.

The present invention is a method for binding a peptide to rhodium, the method comprising steps of:

mixing the rhodium with a solution containing the peptide consisting of an amino acid sequence represented by SEQ ID NO: 01 so as to bind the peptide represented by an amino acid sequence represented by SEQ ID NO: 01 to the rhodium.

Advantageous Effects of Invention

The present invention provides a novel peptide capable for binding to rhodium.

DETAILED DESCRIPTION

Figure 1:
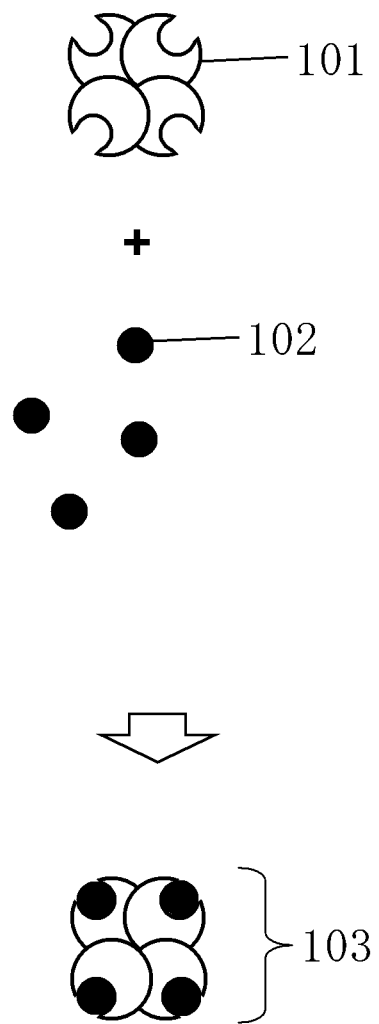
FIG. 1 shows a schematic view of a two-component composite 103 of avidin 101 and biotin-PEG12 (reference number: 102) according to the comparative example 1, which is included in the experiment 1.

The embodiment of the present invention is described below.

The present inventor has discovered that the peptide consisting of the amino acid sequence represented by SQMMGHMGHGNMNHMNHGGKFDFHH (SEQ ID NO: 01) recognizes rhodium. The present invention is provided on the basis of this discovery.

The peptide consisting of the amino acid sequence represented by SEQ ID NO: 01 is derived from the amino acid sequence of the $382^{nd}$ to the $406^{th}$ amino acids of CueO. The term "CueO" means a multi-copper oxidase of *Escherichia coli* K-12 strain.

(Experiment)

The following experiments describe the present invention in more detail.

(Experiment 1)

The experiment 1 is comprised of the example 1 and the comparative example 1.

In the experiment 1, a pull-down method was performed. The pull-down method according to the experiment 1 is easily described below.

In the pull-down method according to the experiment 1, three-component composite of avidin, biotin-PEG12-peptide, and a rhodium nanoparticle is formed in an aqueous solution. After the aqueous solution containing the three-component composite is subjected to a centrifugal separation, three-component composite are not collected as a supernatant. In other words, three-component composite is left in the aqueous solution as a precipitation (i.e., residue). Subsequently, the three-component composite is decomposed by heat treatment, and the solution is subjected to an electrophoresis. After the electrophoresis, a band of the subunit monomer of the avidin is observed.

On the other hand, two-component composite of avidin and biotin-PEG12 is not bound to a rhodium nanoparticle. After an aqueous solution containing the two-component composite is subjected to a centrifugal separation, the two-component composite is eliminated as a supernatant. After the aqueous solution is heated, the aqueous solution is subjected to an electrophoresis. However, since the avidin has been eliminated as one chemical component contained in the supernatant, a band of the subunit monomer of the avidin is not observed.

In the experiment 1, the following solutions were prepared.
Biotin-PEG12-peptide solution
Biotin-PEG12 solution
Tris hydrochloric acid buffer solution
Avidin aqueous solution
Two-component composite aqueous solution of avidin and biotin-PEG12 (See FIG. 1)
Composite aqueous solution of avidin and biotin-PEG12-peptide (See FIG. 2)
Polyoxyethylene (20) sorbitan monolaurate aqueous solution
Buffer solution containing polyoxyethylene (20) sorbitan monolaurate
Sodium dodecylsulfate solution
Glycerol solution
Aqueous solution for an electrophoresis using a denaturing polyacrylamide gel
Rhodium nanoparticle dispersion liquid
A detailed method for preparing these chemical reagents is described below.

(Preparation of a Biotin-PEG12-Peptide Solution)

The present inventor requested synthesis of a compound represented by the following formula (I) (hereinafter, referred to as "biotin-PEG12-peptide") from Sigma Aldrich Japan Co., Ltd. A solid-phase synthesis method was used for the synthesis of the biotin-PEG12-peptide.

(Chem 01)

Biotin-PEG12-SQMMGHMGHGNMNHMNHGGKFD-FHH (SEQ ID NO: 01) (I)

The biotin-PEG12-peptide prepared by Sigma Aldrich Japan Co., Ltd. had a purity of 96.2%.

In the biotin-PEG12-peptide, as is clear from the fomula (I), the N-terminal of the peptide consisting of the amino acid sequence represented by SEQ ID NO: 01 is chemically modified with biotin-polyethylene glycol.

The method for modifying the N-terminal of the peptide with biotin-polyethylene glycol is well known. As one example, EZ-Link NHS-PEG12-biotin (available from Thermo Fisher Scientific Corporation) may be used.

The EZ-Link NHS-PEG12-biotin has the following chemical formula (II).

biotin-PEG12-peptide solution having a concentration of 0.1 mM. The prepared biotin-PEG12-peptide solution was kept under a temperature of −30 degrees Celsius.

(Preparation of the Biotin-PEG12 Solution)

EZ-Link NHS-PEG12-Biotin (available from Thermo Fisher Scientific company) was dissolved with dimethylsulfoxide to prepare an EZ-Link NHS-PEG12-Biotin solution having a concentration of 10 mM.

[Chem 1]

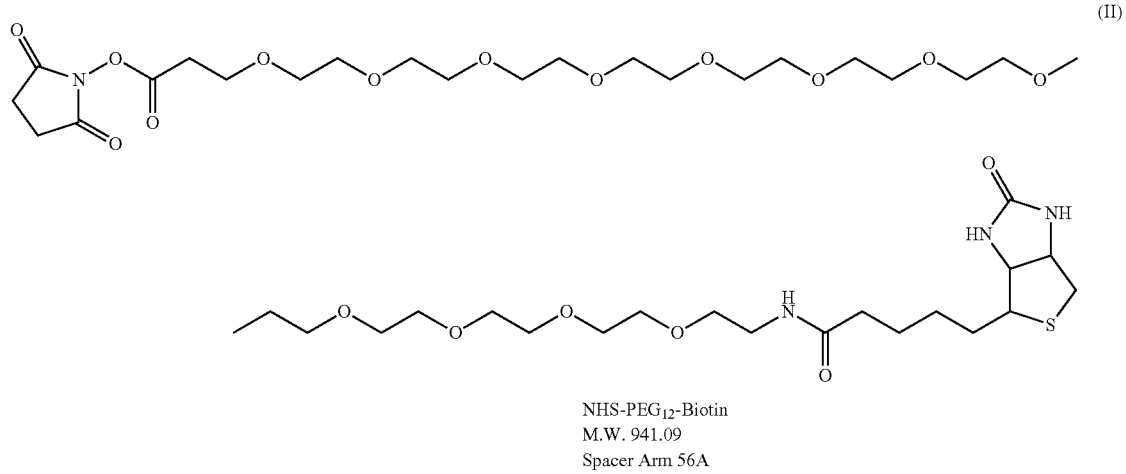

NHS-PEG$_{12}$-Biotin
M.W. 941.09
Spacer Arm 56A

The term "NHS" means N-hydroxysuccinimide. NHS binds to an active ester group. When a peptide is added, the ester group activated by NHS reacts immediately with an $NH_2$ group located at the N terminal of the peptide or the side-chain of a lysine residue to form an amide bond.

The term "PEG" means polyethylene glycol. In more detail, PEG is represented by the following chemical formula (III).

where n is a natural number.

It is desirable that the value of n is not less than 1 and not more than 20. The term "PEG12" means that the PEG where is n=12.

It is believed that the non-specific interaction between two molecules coupled through polyethylene glycol is prevented by the polyethylene glycol. In other words, it is believed that such a polyethylene glycol suppresses the non-specific interaction between two biological molecules chemically bonded to the both ends of the polyethylene glycol. This is because the two molecules are located far away from each other due to the polyethylene glycol interposed between the two molecules, as is clear from the chemical formula (II). For more detail, see Non Patent Literature 1, if necessary.

[Non Patent Literature 1] George et. al., "Effect of Surface Wettability on the Adsorption of Proteins and Detergents", Journal of the American Chemical Society, Vol. 120, pp 3464-3473 (1998)

Therefore, in the chemical formula (I), the biotin molecule and the peptide consisting of the amino acid sequence represented by SEQ ID NO: 01 does not interact with each other due to PEG12.

(Preparation of the Biotin-PEG12-Peptide Solution)

Biotin-PEG12-peptide obtained from Sigma Aldrich Japan Co., Ltd. was dissolved with ultrapure water to prepare a Then, chemical reagents shown in Table 1 were mixed. The mixture liquid was left under a temperature of 25 degrees Celsius for one hour.

TABLE 1

| Chemical reagent | Volume (unit: microliter) |
|---|---|
| 10 mM NHS-PEG12-Biotin | 20 |
| 1M Tris hydrochloric acid buffer solution (pH: 8) | 20 |
| Ultrapure water | 160 |

In this way, the biotin-PEG12 solution having a concentration of 1 mM was prepared. This biotin-PEG12 solution was diluted with water to prepare the biotin-PEG12 solution having a concentration of 0.1 mM.

(Preparation of the Tris Hydrochloric Acid Buffer Solution)

Hydrochloric acid was added in Tris buffer solutions to prepare the following four kinds of Tris hydrochloric acid buffer solutions shown in Table 2.

TABLE 2

| 1M Tris hydrochloric acid buffer solution (pH: 8) |
|---|
| 100 mM Tris hydrochloric acid buffer solution (pH: 8) |
| 10 mM Tris hydrochloric acid buffer solution (pH: 8) |
| 1M Tris hydrochloric acid buffer solution (pH: 6.8) |

(Preparation of the Avidin Aqueous Solution)

Avidin (Available from Thermo Fisher Scientific company, trade name: NeutrAvidin, 10 milligrams) was dissolved with ultrapure water to prepare 10 milligram/milliliter of an avidin aqueous solution. In FIG. 1, the avidin has a reference sign 101.

(Preparation of Two-Component Composite of Avidin and Biotin-PEG12)

The chemical reagents shown in the following Table 3 were mixed. In FIG. 1, the biotin-PEG12 has a reference sign 102. The mixture was left under a temperature of 23 degrees Celsius for two hours.

TABLE 3

| Chemical reagent | Volume (unit: microliter) |
| --- | --- |
| 10 mg/mL of avidin | 50 |
| 1M Tris hydrochloric acid buffer solution (pH: 8) | 5 |
| Ultrapure water | 95 |
| 0.1 mM biotin -PEG12 | 350 |

Subsequently, the mixture (500 microliters) was filtrated using a centrifugal ultrafiltration unit (available from Merck Ltd., trade name: Amicon Ultra-0.5, MWCO: 30,000) to obtain a residue. The centrifugal separation was performed under a temperature of 4 degrees Celsius at an rpm of 10,000×g for 20 minutes. In this way, the mixture was concentrated to obtain a concentrated liquid of approximately 50 microliters.

A Tris hydrochloric acid buffer solution (pH: 8, 450 microliters) having a concentration of 10 mM were mixed to the concentrated liquid. The concentrated liquid was subjected to a centrifugal separation under the same conditions as above again to obtain a concentrated liquid of approximately 50 microliters again. This was repeated once again.

The concentrated liquid was diluted with the Tris hydrochloric acid buffer solution (pH: 8) having a concentration of 10 mM to obtain an aqueous solution containing a two-component composite of avidin and biotin-PEG12. This aqueous solution had a volume of 500 microliter. In FIG. 1, two-component composite of avidin and biotin-PEG12 have a reference sign 103.

(Preparation of Composite of Avidin and Biotin-PEG12-Peptide)

The procedure similarly to that of the preparation of two-component composite of avidin and biotin-PEG12 was conducted, except that the chemical reagents shown in the following Table 4 were mixed instead of the chemical reagents shown in Table 3, so as to prepare an aqueous solution containing a composite of avidin and biotin-PEG 12-peptide.

TABLE 4

| Chemical reagent | Volume (unit: microliter) |
| --- | --- |
| 10 mg/mL of avidin | 50 |
| 1M Tris hydrochloric acid buffer solution (pH: 8) | 5 |
| Ultrapure water | 95 |
| 0.1 mM biotin-PEG12-peptide | 350 |

Figure 2:
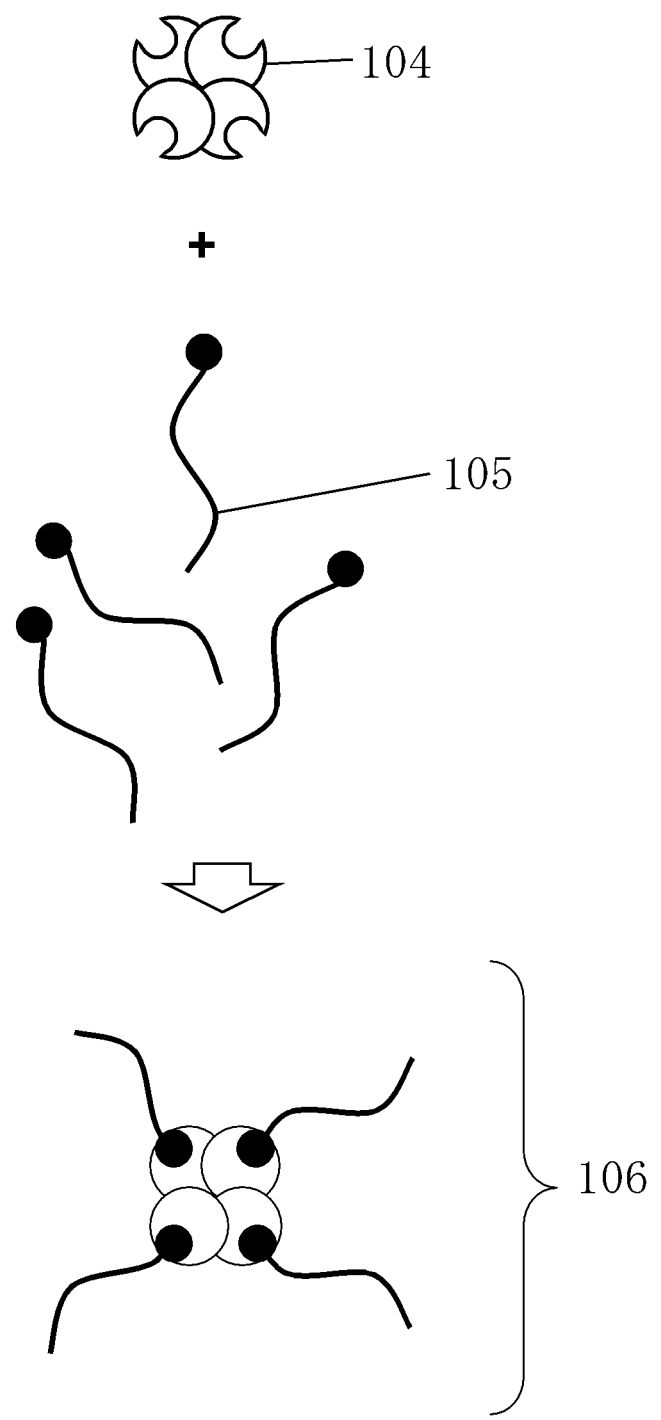
FIG. 2 shows a schematic view of a composite 106 of avidin 104 and biotin-PEG12-peptide 105 according to the example 1, which is included in the experiment 1.

In FIG. 2, the avidin has a reference sign 104. The biotin-PEG12-peptide has a reference number 105. The composite has a reference number 106.

(Preparation of Polyoxyethylene (20) Sorbitan Monolaurate Aqueous Solutions)

An aqueous solution of polyoxyethylene (20) sorbitan monolaurate (available from Affymetrix company, trade name: ANAPOE—20) having a concentration of 10 percent by weight was diluted with ultrapure water to prepare an aqueous solution of polyoxyethylene (20) sorbitan monolaurate having a concentration of 1 percent by weight. Similarly, an aqueous solution of polyoxyethylene (20) sorbitan monolaurate having a concentration of 0.1 percent by weight was prepared. Polyoxyethylene (20) sorbitan monolaurate may be used as a surfactant.

(Preparation of the Buffer Solution Containing Polyoxyethylene (20) Sorbitan Monolaurate)

The two kinds of buffer solutions shown in Table 5 were prepared.

TABLE 5

| Buffer solution |
| --- |
| 10 mM Tris hydrochloric acid buffer solution (pH: 8) containing 0.1% by weight polyoxyethylene (20) sorbitan monolaurate |
| 10 mM Tris hydrochloric acid buffer solution (pH: 8) containing 0.2% by weight polyoxyethylene (20) sorbitan monolaurate |

(Preparation of the Sodium Dodecyl Sulfate Aqueous Solution)

Sodium dodecyl sulfate (available from Wako Pure Chemical Industries Ltd.) was dissolved with ultrapure water to prepare a sodium dodecyl sulfate aqueous solution having a concentration of 10% by weight.

(Preparation of the Glycerol Aqueous Solution)

Glycerol (available from Life Technologies Corporation) was dissolved with ultrapure water to prepare a glycerol aqueous solution having a concentration of 50% by weight.

(Preparation of an Aqueous Solution for an Electrophoresis using a Denaturing Polyacrylamide Gel)

The chemical reagents shown in the following Table 6 were mixed to prepare an aqueous solution. Furthermore, approximately 1 milligram of bromophenol blue (powder) was added to the aqueous solution. Subsequently, the aqueous solution was stirred well. In this way, prepared was the aqueous solution for an electrophoresis using a denaturing polyacrylamide gel.

TABLE 6

| Solution | Volume |
| --- | --- |
| 1M Tris hydrochloric acid buffer solution (pH: 6.8) | 0.55 milliliters |
| 50% by weight glycerol solution | 3.6 milliliters |
| 2-mercaptoethanol | 0.5 milliliters |
| 10% by weight sodium dodecyl sulfate | 4 milliliters |
| Ultrapure water | 1.35 milliliters |

(Preparation of the Rhodium Nanoparticle Dispersion)

A dispersion liquid of the rhodium nanoparticles each having a diameter of 2-6 nanometers (available from Renaissance Energy Research company, 0.5 milliliters) was mixed with ultrapure water (0.5 milliliters).

The mixture was subjected to a centrifugal separation under a temperature of 4 degrees Celsius at an rpm of 290,000×g for 2 hours. Subsequently, the supernatant was eliminated to obtain the concentrated liquid having a volume of 100 microliters. In this way, the mixture was concentrated.

Then, the 0.1% by weight polyoxyethylene (20) sorbitan monolaurate aqueous solution was added to the concentrated liquid. Subsequently, the concentrated liquid was subjected to a centrifugal separation again under the above-mentioned condition to remove the supernatant. In this way, a concentrated liquid having a volume of 100 microliters was obtained.

Again, the 0.1% by weight polyoxyethylene (20) sorbitan monolaurate was added to the concentrated liquid. Subsequently, the concentrated liquid was subjected to a centrifugal separation again under the above-mentioned condition to remove the supernatant. In this way, a concentrated liquid having a volume of 100 microliters was obtained again.

A 0.1% by weight polyoxyethylene (20) sorbitan monolaurate aqueous solution was added to the concentrated liquid to obtain the rhodium nanoparticle dispersion liquid having a volume of 0.1 milliliter.

Example 1

The chemical reagents shown in the following Table 7 were mixed. The mixture was left under a temperature of 25 degrees Celsius for ten minutes.

TABLE 7

| Chemical reagent | Volume (unit: microliter) |
| --- | --- |
| 10 mM Tris hydrochloric acid buffer solution (pH: 8) | 24 |
| 10 mM Tris hydrochloric acid buffer solution (pH: 8) containing 0.2% by weight of polyoxyethylene (20) sorbitan monolaurate | 25 |
| Rhodium nanoparticle dispersion | 50 |
| Composite aqueous solution of avidin and biotin-PEG12-peptide | 1 |

Figure 3:
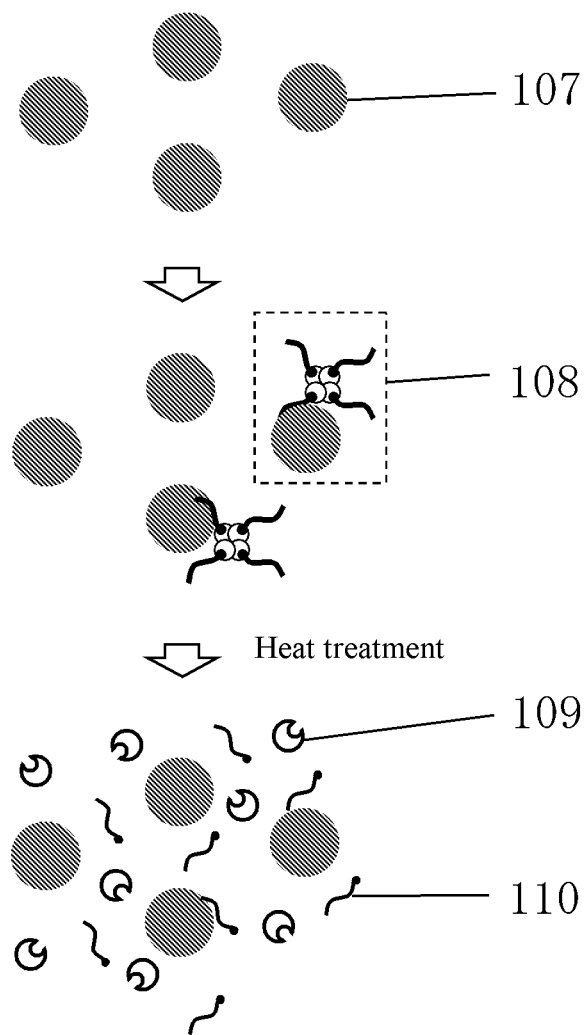
FIG. 3 shows a schematic view of a three-component composite 108 of rhodium nanoparticle 107, avidin 104, and biotin-PEG12-peptide 105 according to the example 1, which is included in the experiment 1.

In FIG. 3, the rhodium nanoparticles have a reference sign 107. The composite of Avidin and biotin-PEG12-peptide have a reference sign 106. The three-component composite of the rhodium nanoparticles, avidin, and biotin-PEG12-peptide have a reference sign 108. The subunit monomer of the avidin obtained by heating the avidin has a reference sign 109. The biotin-PEG12-peptide after the heating has a reference sign 110.

The mixture was subjected to a centrifugal separation under a temperature of 4 degrees Celsius at an rpm of 290,000×g for 30 minutes. Subsequently, the supernatant was removed to eliminate the unreacted biotin-PEG12-peptide. In this way, a liquid mixture was concentrated to obtain a concentrated liquid (i.e., residue) having a volume of 10 microliters.

Then, the Tris hydrochloric acid buffer solution (pH: 8, 10 mM, 200 microliters) containing 0.1% by weight polyoxyethylene (20) sorbitan monolaurate was added to the concentrated liquid. Subsequently, the concentrated liquid was subjected to a centrifugal separation again under the above-mentioned condition to remove the supernatant. In this way, a concentrated liquid (i.e., residue) having a volume of 10 microliters was obtained.

The Tris hydrochloric acid buffer solution (pH: 8, 10 mM, 200 microliters) containing 0.1% by weight polyoxyethylene (20) sorbitan monolaurate was added to the concentrated liquid again. Subsequently, the concentrated liquid was subjected to a centrifugal separation again under the above-mentioned condition to remove the supernatant. In this way, a concentrated liquid (i.e., residue) having a volume of 10 microliters was obtained again. This concentrated liquid was brownish-red. Since a rhodium nanoparticle dispersion liquid is brownish-red, it was confirmed by the naked eyes that the obtained concentrated liquid (i.e., residue) contained rhodium nanoparticles.

The aqueous solution for an electrophoresis using a denaturing polyacrylamide gel was added to the concentrated rhodium particle dispersion liquid. The volume of the aqueous solution was 20 microliters.

Subsequently, an ultrasonic wave was applied to the aqueous solution using an ultrasonic wave washer (available from AS ONE Corporation, trade name: USK-1A, configuration: High).

The concentrated rhodium nanoparticle dispersion was heated under a temperature of 98 degrees Celsius for ten minutes to decompose the avidin molecule to avidin subunit monomers.

After the heating, the concentrated rhodium nanoparticle dispersion was subjected to a centrifugal separation at an rpm of 10,000×g for one minute. In this way, a sample solution according to the example 1 was obtained.

COMPARATIVE EXAMPLE 1

The procedure similarly to that of the example 1 was conducted, except that the biotin-PEG12 was used instead of the biotin-PEG12-peptide. In this way, a sample solution according to the comparative example 1 was obtained.

(Electrophoresis in the Experiment 1)

These two kinds of sample solutions according to the example 1 and the comparative example 1 were subjected to electrophoresis. The detail of the electrophoresis is described below.

A polyacrylamide gel (pre-cast gel, available from Bio-Rad Laboratories, Inc., trade name: 12% Mini-PROTEAN TGX) was equipped to an electrophoresis tank. As an electrophoretic buffer, a pre-mixed buffer (available from Bio-Rad Laboratories, Inc., trade name: premix buffer 10× Tris/glycine/SDS) was diluted ten times with extrapure water. This diluted solution was poured to the electrophoresis tank.

The two sample solutions (for each 15 microliters) according to the example 1 and the comparative example 1 were added to the wells provided at the top of the polyacrylamide gel.

A benchmark protein ladder (available from Life Technologies Corporation, 5 microliters) was added the well provided at the top of the polyacrylamide gel as a molecular weight marker.

The electrophoresis was performed under a constant voltage of 150 volts.

When the Bromophenol Blue contained in the aqueous solution was moved by the electrophoresis to the neighborhood of the bottom of the polyacrylamide gel, the electrophoresis was stopped. Subsequently, a CBB stain was performed with a CBB stain kit (available from Bio-Rad Laboratories, Inc., trade name: R-250 stain & destain kit).

The image of the stained polyacrylamide gel was read with a flatbed scanner (Available from CANON. Inc., trade name: CanoScan D2400U). The band of the subunit monomer of the avidin was quantified using image processing software ImageJ (available from National Institutes of Health) on the basis of the read image.

Figure 4:
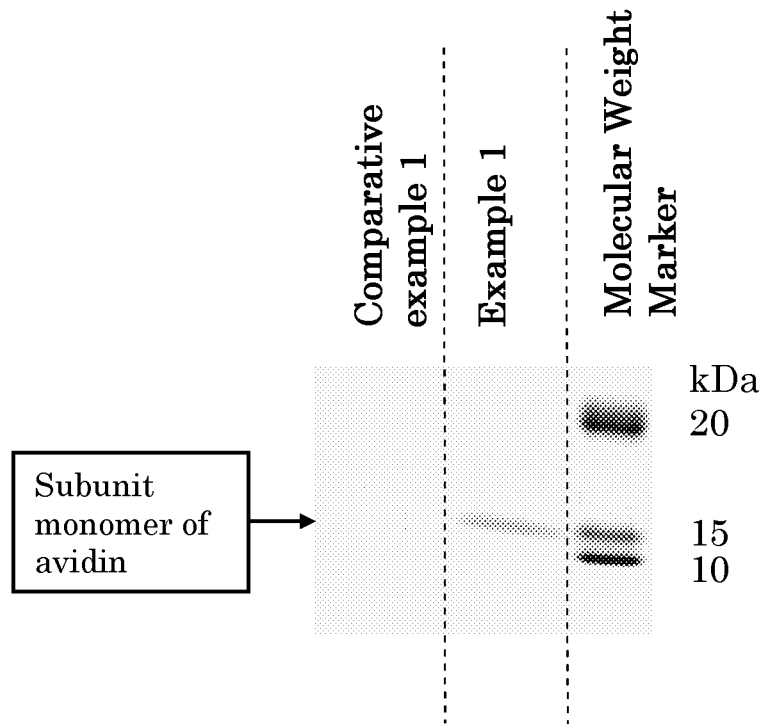
FIG. 4 is an electrophoretic photograph showing the results of the experiment 1.

FIG. 4 shows the electrophoretic results.

As shown in FIG. 4, a clear band was observed in the example 1. On the other hand, such a clear band was not observed in the comparative example 1.

According to the image processing software, the band according to the example 1 contained 38 times as many subunit monomers of avidin as the band according to the comparative example 1.

From the electrophoresis result shown in FIG. 4, namely, the result by a pull-down method, it was found that Biotin-PEG 12-peptide binds to a rhodium nanoparticle to form an aggregate (i.e., precipitate). Since the biotin and the peptide do not interact due to PEG 12, it was found that the peptide consisting of the amino acid sequence represented by SEQ ID NO: 01 binds to rhodium. In other words, it was found that the peptide consisting of the amino acid sequence represented by SEQ ID NO: 01 recognizes rhodium.

INDUSTRIAL APPLICABILITY

The present invention provides a peptide capable for binding to rhodium.

REFERENCE SIGNS LIST

101, 104: avidin
102: biotin-PEG12
103: two-component composite of avidin and biotin-PEG12
104, 110: biotin-PEG12-peptide
106: composite of avidin and biotin-PEG12-peptide
107: rhodium nanoparticle
108: three-component composite of rhodium nanoparticle, avidin, and biotin-PEG12-peptide
109: subunit monomer of avidin

The invention claimed is:

1. A method for binding a peptide to rhodium, the method comprising steps of:
mixing the rhodium with a solution containing the peptide consisting of an amino acid sequence of SEQ ID NO: 01 so as to bind the peptide to the rhodium.

2. A composite comprising a peptide consisting of an amino acid sequence of SEQ ID NO: 01 and rhodium, wherein the peptide is bound to the rhodium.

* * * * *

```
                              SEQUENCE LISTING

<160> NUMBER OF SEQ ID NOS: 1

<210> SEQ ID NO 1
<211> LENGTH: 25
<212> TYPE: PRT
<213> ORGANISM: Artificial
<220> FEATURE:
<223> OTHER INFORMATION: Chemically synthesized
<220> FEATURE:
<221> NAME/KEY: MISC_FEATURE
<223> OTHER INFORMATION: peptide capable for binding to rhodium

<400> SEQUENCE: 1

Ser Gln Met Met Gly His Met Gly His Gly Asn Met Asn His Met Asn
1               5                   10                  15

His Gly Gly Lys Phe Asp Phe His His
            20                  25
```